United States Patent [19]

Sikes

[11] Patent Number: 5,437,618
[45] Date of Patent: Aug. 1, 1995

[54] DEVICE AND METHOD FOR HIP PROTECTION AND STABILIZATION

[75] Inventor: W. David Sikes, Gainesville, Fla.
[73] Assignee: Homeostatics Design Group, Inc., Starke, Fla.
[21] Appl. No.: 306,075
[22] Filed: Sep. 14, 1994

Related U.S. Application Data

[63] Continuation-in-part of Ser. No. 122,076, Sep. 14, 1993, Pat. No. 5,383,920.

[51] Int. Cl.$^6$ .............................................. A61F 5/00
[52] U.S. Cl. ...................................... 602/19; 602/23; 602/24; 607/112
[58] Field of Search .................. 602/19, 23, 24, 13, 602/14, 26; 607/96, 108, 112, 114

[56] References Cited

U.S. PATENT DOCUMENTS

| | | |
|---|---|---|
| 2,889,830 | 6/1959 | Raymond . |
| 4,006,542 | 2/1977 | Larson . |
| 4,573,216 | 3/1986 | Wortberg .............. 2/22 X |
| 4,641,641 | 2/1987 | Strock . |
| 4,858,259 | 8/1989 | Simmons et al. ............. 607/114 X |
| 4,905,678 | 3/1990 | Cumirs et al. .............. 602/19 X |
| 5,027,801 | 7/1991 | Grim ................... 602/23 X |
| 5,062,414 | 11/1991 | Grim ................... 607/108 X |
| 5,113,877 | 5/1992 | Johnson, Jr. et al. ........... 602/27 X |

FOREIGN PATENT DOCUMENTS

| | | |
|---|---|---|
| 0099010 | 1/1984 | European Pat. Off. . |
| 3500078 | 7/1985 | Germany . |
| 8102517 | 9/1981 | WIPO . |

OTHER PUBLICATIONS

Lewinnek, George E. et al. (1980) "The Significance and a Comparative Analysis of the Epidemiology of Hip Fractures" Clin. Orthop. and Related Research 152:35–43.
Cummings, Steven R. et al. (1985) "Epidemiology of Osteoporosis and Osteoporotic Fractures" Epidemiologic Reviews 7:178–208.
Borgquist, L., G. Lindelow, K-G., Thorngren (1991) "Cost of Hip Fracture" Acta. Orthop. Scand. 62(1):39–48.
Consensus Conference, NIH: Osteoporosis (1984) JAMA 252:799–802.
Melton, L. Joseph III et al. (1988) "Lifetime Fracture Risk: An Approach to Hip Fracture Risk Assessment Based on Bone Mineral Density and Age" J. Clin. Epidemiol. 41(10):985–994.
Lotz, J. C., W. C. Hayes (1990) "The Use of Quantitative Computed Tomography to Estimate Risk of Fracture of the Hip from Falls" Bone Joint Surg. 72-A(5):6-89–699.
Lauritzen, J. B., B. Lund (1990) "Impact in patient with hip fractures and in vitro study of the padding effect: introduction of a hip protector" Proceedings of the Danish Orthopedic Society, Oct. 27–28, 1989 in Acta Orthop. Scand. 61(Suppl. 239):11.
Jarnlo, G.-B., K.-G., Thorngren (1991) "Standing balance in hip fracture patients" Acta. Orthop. Scand. 62(5):427–434.

*Primary Examiner*—Linda C. M. Dvorak
*Attorney, Agent, or Firm*—Saliwanchik & Saliwanchik

[57] ABSTRACT

A novel joint protection device is disclosed having a rigid outer shell and at least one cushioned pad on its inner face. The device is placed next to the joint area being protected. The cushioned pad is a cushioning foam material, or inflatable, or gel-filled for deflection or absorption of the forces encountered upon an impact. The device can be used for a novel method for prevention of joint injury, especially injuries sustained by the elderly due to falls. The novel device is also provided with a belt and a gluteus medius pad for advantageously stabilizing the hip joint.

24 Claims, 5 Drawing Sheets

DEVICE AND METHOD FOR HIP PROTECTION AND STABILIZATION

CROSS-REFERENCE TO A RELATED APPLICATION

This is a continuation-in-part of application Ser. No. 08/122,076, filed Sep. 14, 1993, now U.S. Pat. No. 5,383,920.

BACKGROUND OF THE INVENTION

Fractures of the proximal part of the femur are an important public-health problem and a major source of mortality and morbidity among the elderly. The incidence of fractures of the hip increases exponentially with age, beginning at about forty years for women and forty-five years for men, and rising at eighty years to an aggregate rate of between 20 and 30 percent for women and between 10 and 15 percent for men. Consequently, nearly one of three women and one of six men could sustain a fracture of the hip by the age of ninety years. Lewinnek, G. E., J. Kelsey, A. A. White III, N. J. Kreiger (1980) *Clin. Orthop.* 152:35–43. This problem is expected to worsen with the projected increase in the average age of the world population. Some researchers have posed the possibility of a two- to three-fold rise in the total number of such fractures by the middle of the next century. Cummings, S. R., J. L. Kelsey, M. C. Nevitt, K. J. O'Dowd (1985) *Epidemiol. Rev.* 7:178–208.

Hip fracture in the elderly is currently the largest diagnostic group treated in hospital orthopedic departments. Estimates of costs of hip fractures have been calculated for inpatient treatments in the acute phase; however, little is known today about the economic consequences of the entire rehabilitation process. Borquist, L., G. Lindelöw, K.-G. Thorngren (1991) *Acta. Orthop. Scand.* 62:39–48. Thus, prevention of hip fractures can significantly contribute to the reduction of health care costs which are currently of primary concern.

There is considerable controversy as to whether fracture of the hip should be regarded as a disease-related injury resulting from excessive loss of bone, i.e., osteoporosis, or as an accident-related injury due to frequent or severe trauma. See Consensus Conference, NIH: Osteoporosis (1984) *JAMA* 252:799–802. Although the strong effect of bone density on the risk of fracture of the hip has been widely substantiated, the true influence of this variable is confounded by the increased propensity for falls and injury in the elderly. The combination of both appear to be contributing factors among the elderly. Melton et al. concluded that the combination of reduced skeletal resistance to trauma and increased propensity for falling is an important determinant of risk (Melton, L. J., S. H. Kan, H. W. Wahner, B. L. Riggs [1988] *J. Clin. Epidemiol.* 41:984–985). As a result, it appears that both loss of bone and trauma are causes of these age-related fractures.

Prior attempts to reduce the incidence of age-related fractures of the hip focused primarily on the prevention or inhibition of the excessive loss of bone associated with osteoporosis. It is now understood that factors in addition to loss of bone play an important role in the etiology of fracture of the hip. Previously, the process of fracture has been poorly understood, particularly with regard to the magnitude and direction of the loads that are present during the impact of a fall. Lotz et al. conducted an in vitro investigation of the loads and energies needed to fracture the proximal part of the femur. They found fracture loads ranged from 778 to 4,040 newtons. Lotz, J. C., W. C. Hayes (1990) *J. Bone Joint Surg.* 72-A:689–699.

A Danish group of researchers also investigated the role of falls as a cause of hip fractures and concluded that nearly all hip fractures seemed to be caused by trauma. Lauritzen, J. B., B. Lund, Proceedings of the Danish Orthopedic Society, Oct. 27–28, 1989 in *Acta. Orthop. Scand.* (1990):61 (Suppl.239). Sagittal postural sway has been implicated as a contributing factor in loss of balance, contributing to falls which can potentially result in a hip injury. Jarnlo, G.-B., K.-G. Thorngren (1991) *Acta Orthrop. Scand.* 62(5):427–434.

BRIEF SUMMARY OF THE INVENTION

The subject invention concerns a unique device for protection of a joint and the area surrounding the joint, e.g., the hip. For purposes of this invention, the term "joint" refers to the articulatio, i.e., the juncture of at least two bones, and the surrounding area of the articulatio. The subject device is a protective pad device which can be placed at a position lateral to the area of body in need of protection. For example, the device can be placed lateral to the trochanter or femoral head area of the hip, whereby the protective device provides a means for preventing or reducing the risk of hip injury, including femoral head or neck fracture. The subject device for the protection of the joint and surrounding area comprises at least two components, specifically, the outer component which faces away from the body and the inner component which faces toward the body when the device is in use.

The outer component comprises a rigid outer shield having an outer and inner face. The outer shield preferably has a curved shape substantially conforming to the shape of the body where the device is positioned when used. This substantially curved shape provides a convex, rigid outer surface and a concave inner face. The concave inner face can have at least one rib as a reinforcement of the outer shield.

The rigid outer surface can deflect or absorb the force of an impact sustained by a fall or other direct contact with a hard surface. The outer shield component can have a means for connecting a securing means, e.g., a strap or belt, to the shield in order to hold the joint protection device in place. In one embodiment, the strap can be connected to a flange integrally formed at opposite ends of the outer shield. The flange can have apertures or slots in order to receive a strap or a connecting means for affixing the strap thereto. Other embodiments can employ more than one device to protect more than one joint, simultaneously. Further, it would be understood that the protection device can be held in the appropriate position by other securing means which can include specialized pockets formed in clothing in order to hold the device in place.

The device also comprises at least one cushioned pad disposed on the inner, concave face of the outer shield. The cushioned pad can be a foam material or can be a bladder filled with air, liquid, or a gel-like substance or can be compartmentalized and be filled with a combination of these or other materials which can provide cushioning for protection or comfort. The cushioned pad can be permanently or detachably affixed to the outer shield by any appropriate attachment means. Preferably, the cushioned pad is permanently affixed by an adhesive composition disposed between the cushioned pad and the rigid outer shield.

In one embodiment, the cushioned pad has a peripheral pad component, and a central pad component which can reduce discomfort to the wearer of the device. In another embodiment, the pad component includes a pad which applies pressure to the gluteus medius muscle, thereby resulting in further joint stabilizing advantages.

The subject invention also concerns a method for using the hip protection device. The method comprises placing the device in a position next to the body so that the cushioned pad is positioned over the trochanter area of a hip joint and holding the pad in that position by a securing means. In one method, a securing means, e.g., a belt or strap, can be affixed to opposite ends of the pad device, whereby the belt, or belt segments interconnected with the device, can completely encircle the body at the hip or pelvic area. Placement of the protection devices at each hip and strapping the devices together so as to completely enstrap the wearer around the pelvic area is also advantageous. This method serves to hold the hip joints in place, thereby providing a method for stabilizing the hip joint, i.e., reducing postural sway.

Thus, it is an object of the invention to provide a convenient, lightweight, and durable protection device and method for using the device to prevent injury to the hip or other joint area of the body similarly susceptible to injury due to impact. It is a further object of the invention to provide a means for stabilizing the hip joint to further facilitate the protection of the hip and prevention of injury thereto.

BRIEF DESCRIPTION OF THE DRAWINGS

The particular features and advantages of the invention, as well as other objects and embodiments, will become apparent from the description provided herein, taken in connection with the accompanying drawings, in which a preferred embodiment is shown.

DETAILED DISCLOSURE OF THE INVENTION

Figure 1:
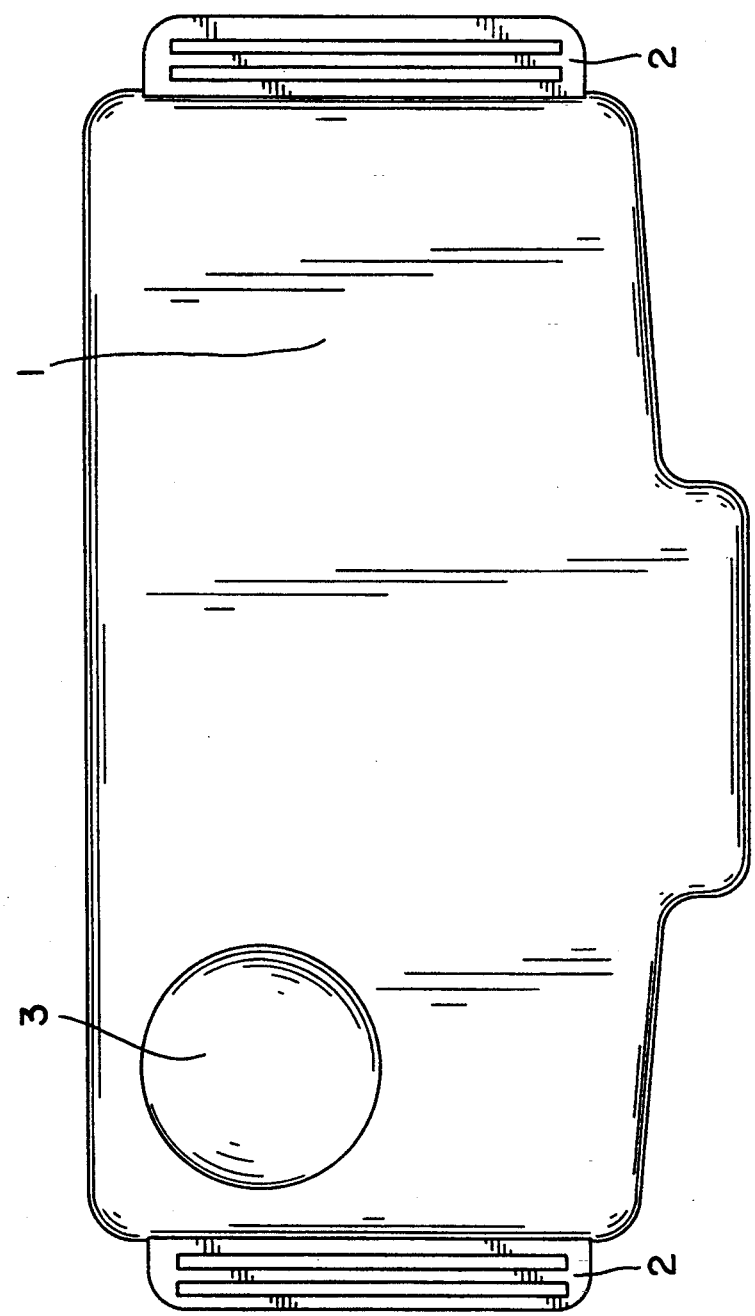
FIG. 1 is a front view of the outer face which is positioned away from the body when in use. This view of the joint protection device shows the rigid outer shield 1, the slotted flange for attaching a strapping means 2, and the inflation pump valve 3.

The subject invention concerns a novel device and method of use for protection of a joint and the area surrounding the joint susceptible to injury by direct contact with a hard surface. The device is a protective, cushioned pad which, in a preferred embodiment, can be placed over the femoral head or trochanter area of the hip and, when placed in this position, can protect the hip against injury, e.g., fracture of the femoral head or neck due to a fall or other impact with a hard surface. In a preferred method of use, two devices can be used—one device being placed lateral to each of the left and right trochanter areas. The two protection devices are connected or held in place by a securing means, e.g., by a strap or belt. The strap or belt can be adjustably tightened around the hip to hold the joint protection device in place. The tightening of the belt around the hip can also advantageously serve to hold the femoral head in its socket, which thereby stabilizes the hip joints and prevents postural sway, especially sagittal postural sway, i.e., postural sway in the sagittal plane. Stabilizing the hip joints can contribute to maintaining of balance by a person having loose or stretched tendons or ligaments in the hip joint area, e.g., an elderly person or person sustaining an injury to the hip in an accident. This maintenance of balance therefore also prevents falls from occurring, which can further reduce the risk of injury due to a fall.

Numerous alterations of the device and method herein disclosed will suggest themselves to those persons of ordinary skill in the art. However, it is to be understood that the present disclosure relates to the preferred embodiment of the invention which is for illustrative purposes only and not to be construed as a limitation of the invention. All such modifications which do not depart from the spirit of the invention are intended to be included within the scope of the appended claims.

In a preferred embodiment, the joint protection device is a hip protection device which comprises a cushioned pad component disposed on the inner face of a rigid outer shield. The first cushioned pad can preferably be centrally disposed on the inner face of the rigid outer shield so that the centrally disposed pad is positioned directly over the trochanter area of the hip or proximal end of the femur when in use. The second cushioned pad component can correspond substantially to the size and shape of the outer shield disposed so that it substantially surrounds the central pad. This second pad component is herein referred to as the peripheral pad component. In the preferred embodiment, the centrally disposed cushioned pad component is a gel-filled bladder and the peripheral pad component is an inflatable or air-filled pad. More preferably, the peripheral pad component has a thickness greater than the centrally disposed pad component, giving the effect of a recessed central pad component when the peripheral pad is inflated. Advantageously, the central pad is lifted away from the body so that it does not come in direct contact therewith when the joint protection device is worn in its normal position. The inflatable pad component can be provided with a valve or pump as a means for inflating or deflating the pad. The cushioned pad(s) can be permanently or temporarily affixed to the rigid outer shield or its covering. In the preferred embodiment, the cushioned pad can be permanently affixed to the rigid outer shield with an adhesive disposed therebetween. The adhesive can be any appropriate adhesive or cement as accepted in the art.

The subject invention can perhaps be best understood by reference to the drawings which show a preferred embodiment of the invention. Referring now to FIG. 1, the joint protection device or, as can be referred to herein a hip protection device, is shown to comprise an outer shield 1 of substantially rigid material. As shown, the device can be substantially rectangular in shape, having an outer planar or concave face which faces away from the body. The outer shield can have other shapes as desired, including square, ovoid, or irregular shape, so long as it provides an outer face which can sustain an impact with a hard surface, and an inner face whereupon a cushioned pad can be disposed. The outer face of the outer shield can be substantially planar or flat, and can be provided with grooves or indentations for advantageously guiding or disposing a strap or belt therearound. In addition, a means for engaging a strap or belt or for securing the belt or strap in place can also be provided on the outer planar face. For example, a hook and loop material, e.g. VELCRO, can be placed on opposing faces of the outer shield and strap so that the strap and the outer shield of the hip protection device can be detachably engaged.

The outer shield can be any rigid material which can deflect or absorb a force encountered during an impact with a hard surface. For example, wood, metal or alloy, natural or synthetic rubber, ceramic, leather, paper, plastic, composite or resinous polymer, including a thermoplastic, and the like, can be used to make the rigid outer shield. In one embodiment, the outer shield can be a laminated composition wherein an outer layer of the rigid material as described above, can be disposed as a covering over an inner core of a lightweight material. For example, the lightweight core can comprise a cushioned sponge or foam material, e.g., polyurethane, styrofoam, or other similar lightweight material. Preferably, the core comprises a material which can also absorb the shock or force of an impact to contribute to the functionality of the joint protection device. In another embodiment, the rigid outer shield can be formed so that the inner face has at least one rib for reinforcement. In a preferred embodiment, the rigid layer of the outer shield can be a thermoplastic outer layer e.g., shaped memory polymer (Memory Technologies, Inc.) or Plastazote (BXL Plastics, Ltd.) covering a polystyrene core. The outer surface of the rigid layer can also be covered with a padded layer of a polyurethane cushion material, e.g., PPT.

Using a thermoplastic for the rigid outer shield component of the subject invention can enable a person to shape or mold the device to fit an individual user or wearer of the device. For example, the joint protection device can be initially provided as a substantially flat device, advantageously facilitating shipping and packaging of the device. The device can then be heated to become temporarily flexible enough so that the device can be shaped, molded, or contoured to substantially conform to the shape or contour of the body of the wearer. Upon cooling, the shield again can become rigid and inflexible, and is thereby custom-formed or fitted to the particular wearer. This provides the advantage of having the device fitted specifically and individually to the wearer which can optimize comfort and protection.

Figure 2:
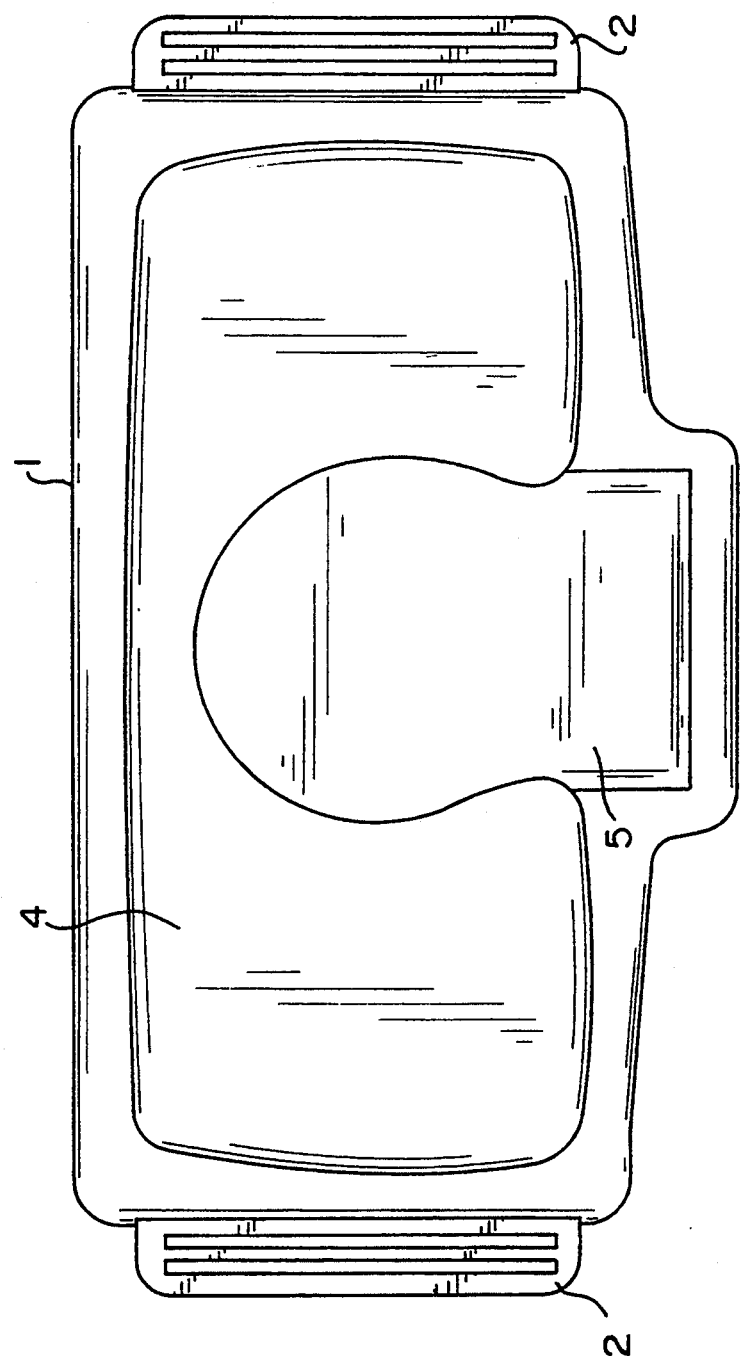
FIG. 2 is a front view of the inner face which is positioned next to the body when in use. This view of the joint protection device shows the rigid outer shield 1; the slotted flange 2 for attaching a securing means, e.g., a strap or a belt; the peripheral cushioned pad 4; and the central cushioned pad 5.
Figure 3:
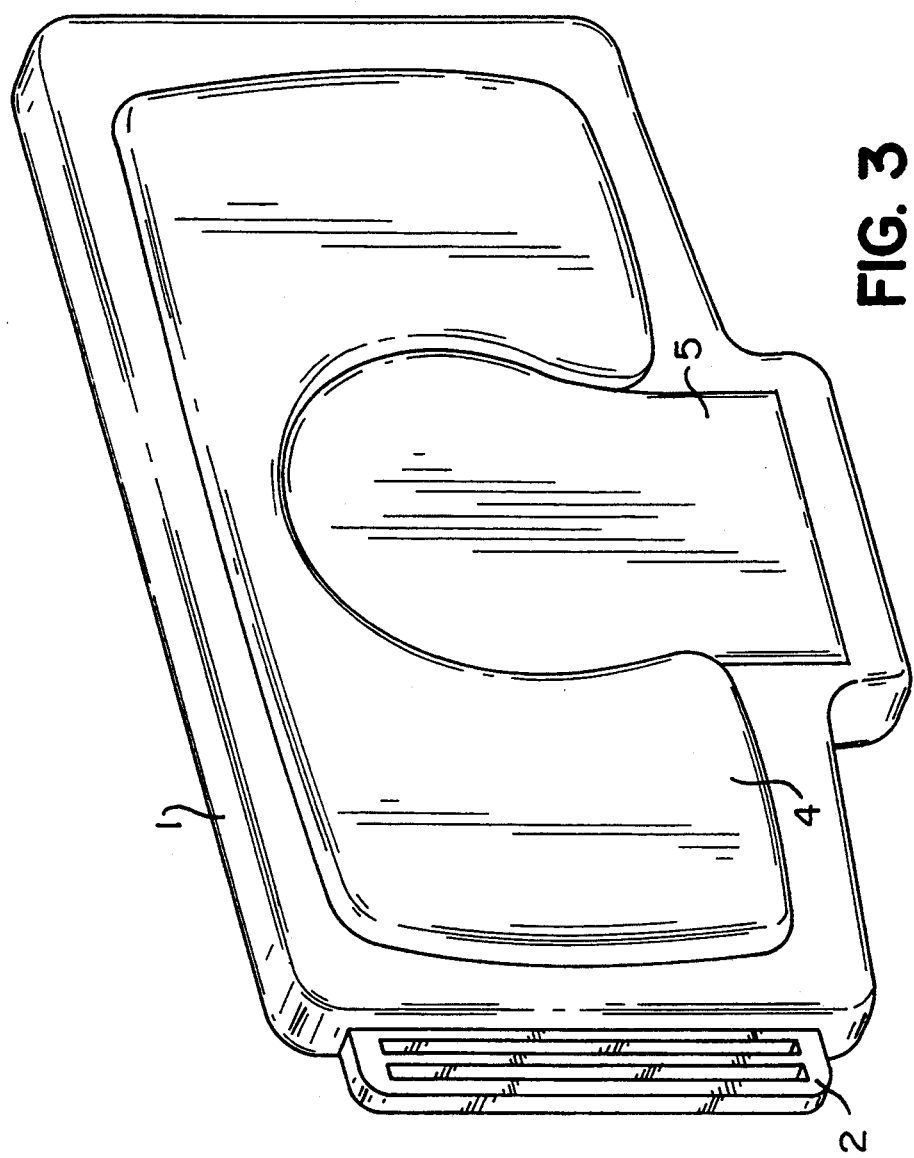
FIG. 3 is a perspective view of the subject joint protection device showing the inner face which is positioned next to the body when in use. Shown here is the device comprising the components of the preferred embodiment, namely, the outer shield 1, the slotted flanges 2, the peripheral inflatable cushioned pad 4, the central gel-filled cushioned pad 5, and the inflation pump valve (shown in phantom view).
Figure 4:
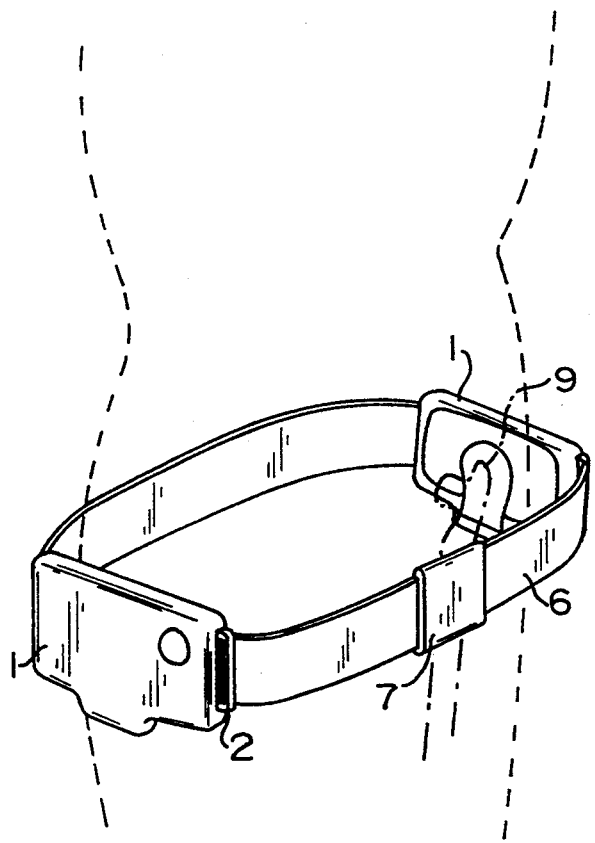
FIG. 4 shows the preferred method for using the subject joint protection device. Specifically shown is the use of two joint protection devices, i.e., a joint protection device for the right and left hip joint, each device having its central pad placed lateral to the femoral head for the protection of the hip 9. Also shown are the two hip protection devices connected by a strapping means 6, e.g., a belt, affixed to the slotted flange. The belt is adjustably tightened or loosened by the buckling means 7.
Figure 5:
FIG. 5 shows an embodiment of the joint protection device wherein a gluteus medius pad 10 is included. The pad components 4 and 5 disposed on the inner face of the outer shield 1 is shown in a sectional view in order to reveal the internal ribs 11, formed as part of the inner face of the outer shell.

FIG. 2 shows the inner planar face of the outer shield on which is disposed a central pad 5 and a peripheral pad 4. These pads are placed toward the body when the joint protection device is in use. Preferably, the peripheral pad is inflatable having a pump valve integrally connected thereto; the central pad is preferably gel-filled. The central pad can be positioned lateral to the trochanter area or the femoral head when the protection device is in its preferred position of use (see FIG. 4). Preferably, the centrally disposed cushioned pad can be substantially "key hole" shaped, i.e., having a substantially circular top portion and having at the bottom of the circular portion a rectangular portion forming a neck which extends toward the distal end of the femur when the pad is correctly positioned next to the body, as shown in FIG. 4. The central pad can be a foam rubber or foam latex or other polymer core or preferably can be a polymer bladder filled with air or a liquid or gel-like material. The pad can further have a covering on a face of the pad which is positioned toward the body, wherein the covering comprises a material which reduces irritation when in contact with the skin for extended periods.

It should also be understood that the cushioned pads can be inflated or filled with other compositions, so long as the composition is compatible with the material used in making the cushioned pad. Standard practice would suggest that a fluid can be used to fill the bladder of a cushioned pad wherein a "fluid" is understood to be a gas or liquid or a semi-solid or gel. Although preferred material for filling the central pad is a gel, e.g., a silicone gel (available from Dow Chemical Co., Midland, Mich.), the bladder can alternatively be filled with air, a known mixture of gases, or a single gas, e.g., nitrogen. It is preferable to use a nonflammable gas. Alternatively, a liquid can be used to fill the bladder, e.g., water, saline, or other non-aqueous liquid compatible with the pad material. The liquid can be of a viscosity which ranges from that approximating water to an aerogel, semi-solid, or other gel-like material. In addition, a solid, e.g., foam rubber or other resilient material, can be used so long as the desired cushioning effect is produced.

Disposed around the perimeter and periphery of the central pad, the subject joint protection device can have a second cushioned pad herein referred to as a peripheral pad. The peripheral pad can preferably be an inflatable bladder 4. The outer perimeter of the second bladder component can substantially conform to the shape of the perimeter of the outer shield. Any airtight or watertight inflatable material can be used for making the bladder. However, it is preferred to use a vinyl impregnated nylon to provide appropriate durability. Also provided as part of the inflatable bladder is a valve or pump 3 for inflating and deflating the bladder. Inflation/deflation pump valves are well-known in the art and are readily adaptable for use with the subject invention. In the preferred embodiment, a "pump" valve system can be provided which allows the wearer to inflate the bladder with ambient air. This type of valve system includes a one-way intake valve which inflates the bladder as it is "pumped" and a release valve which allows for deflation of the bladder. In a preferred embodiment, the peripheral cushioned pad can be made so that the wearer can inflate or deflate the bladder as desired by the regulation of the internal pressure in the pad. This permits the wearer to adjust the cushion effect according to the load or according to the desired appearance. For example, if maximum cushioning is desired, then the cushion can be fully inflated. On the other hand, the pressure can be regulated in the bladder so that the pad is less prominent beneath the clothing. The air-filled compartment can be permanently filled by filling the compartment to the desired pressure and permanently sealing the pad. Similarly, liquid- or gel-filled pads can be made to remain substantially permanently filled. In the preferred embodiment, the outer shield can be provided so that an aperture is formed therein wherein the position of the aperture corresponds to the position of the valve so that the valve can extend through or be accessed by the user through the outer rigid shield.

Preferably, when inflated, the peripheral pad has a thickness which is substantially more than the thickness of the central pad component. The "thickness" of the cushioned pads would be readily understood to refer to the distance from the inner face of the outer shield to the face of the cushioned pad which can contact the body. The internal pressure of the inflated peripheral pad is maintained at a level to provide for its greater thickness as compared to the central pad, effectively creating a recessed central pad wherein the recessed central pad is held away from the body by the inflated peripheral pad, which minimizes contact between the body and the central pad. Keeping the central pad away from the body advantageously results in reduced friction and irritation at the juncture, i.e., point of motion, of the joint. This unexpected advantage can improve the comfort and wearability of the protection device, thereby increasing its ability to provide protection against hip injury.

A cushioned pad for use with the subject joint protection device can be constructed from any air-tight or liquid-tight material which can be formed into a bladder. In one embodiment, the pad can be constructed of two plies which are sealed around the perimeter, and in which the two plies form a bladder or cell which defines a hollow compartment. Separate cells within the bladder can then be formed by dividing the bladder, the divisions being formed by a stamping procedure which seals the upper and lower plies together at a linear juncture. The individual inflatable cells can also be formed separately, interconnected at one end by a flow channel, and held together by material conformed to house and completely and closeably surround the inflatable tubes and flow channel. It is obvious that any appropriate edge binding can be used, including stitching. An advantage of such binding can include function as well as appearance in that the possibility of separation and, therefore, leakage, can be substantially reduced. Any appropriate adhesive, e.g., glue, heat seal, and the like can be used to permanently seal the seams of the pad or to permanently affix a pad component to the outer shield. The coverings of the pads can also be permanently or detachably affixed.

As additionally shown in FIGS. 1 and 2, at opposite positions on the perimeter of the subject device a slotted flange I can be provided for engaging a securing means. In a preferred embodiment, the securing means is a strap or belt which can be a webbing material. Preferably, the slotted flange comprises two slots each having its length slightly larger than the width of the belt so that the belt can be easily looped through the slots. As shown in FIG. 4, the belt can be engaged to the slotted flange by being looped therethrough and permanently or detachably affixed to itself by stitching, by hook and loop material, or any known or similar fastening device.

The belt can further be provided with a buckling means 7. The methods and types of devices which can be used for the buckling means would be readily apparent to a person of ordinary skill in the art. These other methods of engaging the strap and other buckling means which are not specifically exemplified herein are also intended to be part of this invention. For example, the securing means can be a single belt or strap which can be wrapped completely around both the body and the device. Alternatively, the securing means can comprise more than one belt which can link two hip protecting devices together (see FIG. 4). This embodiment essentially forms a single device comprising two belts and two hip protection devices which can completely encircle the pelvic area in order to keep the hip protection devices in place.

In one embodiment, the cushioned pad component is, in cross-section, a tiered, cushioned padding material having the portion of the cushioned pad which is to be positioned directly over the trochanter area (the central pad component) recessed in relation to the pad component which is peripheral to the central pad component. One advantage of a cross-sectionally tiered pad is that the central and peripheral pad components can be easily formed by molding a single pad having a raised peripheral component and the recessed central pad component.

In another embodiment of the invention, the apertures or slots formed in the flange can be substantially circular in order to receive multiaxial hinges, or chaffes, which can be engaged to the flange to affix the belt thereto. Preferably, the substantially circular slots are provided as a plurality of apertures on the flange which provide a means for adjusting the position of the belt. For example, when two cushioned pad devices are used-one for each hip joint-it has been observed that positioning two belts, one across the front of the wearer and one across the back of the wearer, wherein the front belt is placed at the uppermost position and wherein the back belt is placed at the lowermost position, can increase the pressure applied and facilitates the secure placement of the pads. This positioning of the belts can be achieved by affixing the front belt chaffes to the uppermost apertures on the ventral flange and affixing the back belt to the lowermost apertures on the dorsal flanges. The result of this positioning of the front and back belts is greater freedom of movement for the wearer without disturbing the placement of the central pad component over the trochanter area of the hip. In addition, positioning the belts in this manner advantageously stabilizes the hip joint of the wearer by buttressing the lumbopelvic arch.

In a further embodiment of the invention, the cushioned pad is formed such that a third tier is present which is further raised in relation to the central and peripheral pad components. When the protective device is placed on the wearer, this first pad component is on the top, or cranial, side of the device and protrudes medially, just above the trochanter area at the position of the gluteus medius muscle. The third tier pad component is accordingly termed the gluteus medius pad component for purposes of the subject invention. The gluteus medius pad, alternatively, can be formed as a separate pad. Typically, the gluteus medius pad component protrudes approximately one-half inch higher than the peripheral pad component but can vary according to need or what may be desired for optimal comfort. The gluteus medius pad effectively increases the load (and thus, tone) of the gluteus medius muscle which augments lateral abduction, reverses medial abduction (adduction), and thereby can stabilize the articulation of the hip joint.

The securing means can be a belt comprising a woven, natural, or synthetic fabric, e.g. cotton or nylon, which can be adjustably and conveniently fastened by the wearer by a commonly known buckle. The belt can alternatively be an elastic or stretchable material which can be stretched in order to place the belt in the correct position and which can return to its original shape and size by elastic force.

In addition, the belt can have a covering or liner disposed on either of its faces. Preferably, the belt can have a covering disposed on its inner face which can reduce friction or irritation when in contact with the skin of the wearer. A preferred material which can be used for the covering contacting the body is any fabric e.g., nylon, which can resist moisture, especially perspiration from the body. More preferably, a fabric can be used which has a wicking property which can draw moisture away from the body. For example, ULTRILURE (available from Langer Biomechanics Group, Inc., Deer Park, N.Y.) can be used as a contact surface on the belt or any contact surface of the joint protection device.

For additional comfort and further reduction of irritation, the ULTRILURE can be provided with a cushioned backing disposed between the ULTRILURE contact surface and the device component. The cushioned backing can be any cushion material, but is preferably a viscoelastic, foam rubber, foam latex, sponge rubber, neoprene sponge, vinyl sponge, or a like sponge comprising a synthetic or natural polymer. Most preferably, the cushion material is a polyurethane, which is readily available as PPT from Langer Biomechanics Group, Inc. PPT is known to have antibacterial and antifungal properties which are advantageous to reduce odor and irritation. Other materials which can be used as a foam cushion backing are SORBOTHANE, SPENCO, Medical Grade PORON, and DCS. These materials are known materials commonly used in the manufacture of orthopedic devices, especially pads for shoe cushions.

Furthermore, the cushioned pads and general technology described herein can as well be utilized and easily adapted for use as pads for protection of other joints, e.g., elbow or knee pads used by athletes such as football or hockey players, skiers, and the like. It should further be understood and apparent that any of the surfaces of the joint protection device which can come into contact with the skin of the wearer can have a non-irritant material disposed on the face which contacts the body.

Following are examples which illustrate procedures, including the best mode, for practicing the invention. These examples should not be construed as limiting.

EXAMPLE 1

Embodiments of Pad Materials and Construction

Materials and procedures involved in the construction of the subject invention can vary with respect to whether the cushioned pad is of a single-component or multiple-component construction. For purposes of this invention, "multiple" means more than one, typically two, but as many as twenty or more. In a single-component construction of the subject cushioned pad, a single type of material is molded or formed into a desired shape of the pad wherein the molded or formed material defines the bladder. A preferred shape of the bladder is shown in FIG. 1. The material used is typically a polymer, rubber, or any like material which has the desired characteristics of being non-porous, or air-tight, and capable of forming a seal which will contain the filler substance. The material may also preferably be sealable to itself, e.g., a plastic or polymer which can be heat-sealed, sealed with stitching, or by applying an adhesive. Divisions can also be made in the bladder to separate the hollow compartment into more than one compartment. The divisions can be made by stamping procedures known in the art, heat-sealing, or by applied adhesives as disclosed above.

Other constructions can employ the use of more than two materials. For example, the bladder forming the peripheral cushioned pad can be constructed separately from the pad forming the central pad. Either one of the pads can be filled with air or a gel. The bladder is preferably constructed as a single or two component bladder of opposing faces, as described above, and the materials comprising the bladder can be different from one another.

EXAMPLE 2

Method for Custom Formed Protection Device

In a preferred embodiment of the subject invention, the hip protection device can be molded to conform to the shape of the body surface of an individual patient's hip area. This is advantageous for reasons which include, inter alia, comfort and aesthetics for the patient, and convenience for the manufacturer or packager to provide a substantially flat product for reproducibility and for packaging purposes. The outer shield, comprising a thermoplastic material, can be heat-molded according to procedures which would be recognized in the art by ordinarily skilled artisans. For example, the subject joint protection device can be removed from its package, heated to about 45° C. with a hand-held heater or dryer device, placed in the appropriate position as worn by the patient, and hand-molded to the desired shape. The thermoplastic is allowed to cool, and the subject device is thus custom formed to an individual patient. The form fitting procedure can be repeated as desired.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A device for the protection of a joint and surrounding area against an injury due to contact with a hard surface, wherein said device comprises an outer rigid shield having an outer and inner face, a cushion comprising a plurality of cross-sectionally tiered pad components affixed to the inner face of said shield wherein said plurality of pad components comprises a first pad component centrally disposed on the inner face of said shield, a second pad component disposed around the periphery of said first pad component, and a third pad component disposed cranially to said first and second pad components, wherein said second pad component has a thickness greater than said first pad component wherein said second pad component is adapted to directly [contacts]contact a wearer of said device in use, thereby holding said centrally disposed first pad component away from the wearer, and wherein said third pad component protrudes medially beyond the first and second components so as to apply pressure to a gluteus muscle of the wearer when in use.

2. The device, according to claim 1, wherein said device is positionable so that said third pad component applies pressure to a gluteus medius muscle.

3. The protection device, according to claim 1, wherein said device further comprises a securing means for holding the device in place next to a joint area of a body.

4. The protection device, according to claim 3, wherein said securing means is an adjustable belt.

5. The protection device, according to claim 3, wherein said outer rigid shield further comprises a connecting means for connecting the securing means to said device.

6. The protection device, according to claim 5, wherein said connecting means comprises a slotted flange.

7. The protection device, according to claim 1, wherein said rigid outer shield comprises a reinforcement rib on the inner face of said shield.

8. The protection device, according to claim 1, wherein a layer of sponge material covers said plurality of pad components.

9. The protection device, according to claim 8, wherein the sponge material is selected from the group consisting of viscoelastic, latex foam, sponge rubber, neoprene sponge, vinyl sponge, and polyurethane sponge.

10. The protection device, according to claim 8, wherein the sponge material has a further layer of fabric disposed on the side of the sponge adapted to be placed next to the body.

11. The protection device, according to claim 10, wherein said fabric has a moisture wicking property to draw moisture away from the body.

12. A method for prevention of injury to a joint or an area of a body surrounding the joint, said method comprising placing next to the joint or surrounding area a protection device, wherein said device comprises an outer rigid shield having an outer and inner face, a cushion comprising at least one pad component disposed on the inner face of said shield, a second pad component disposed around the periphery of said first pad component, and a third pad component disposed cranially to said first and second pad components, wherein said second pad component has a thickness greater than said first pad component whereby said second pad component directly contacts a wearer of said device, holding said centrally disposed first pad component away from the wearer, and wherein said third pad component protrudes medially beyond the first and second Fad components to apply pressure to a gluteus muscle of a wearer.

13. The method, according to claim 12, wherein said gluteus muscle is a gluteus medius muscle.

14. The method, according to claim 12, wherein said method further comprises holding the protection device in position by a securing means.

15. The method, according to claim 12, wherein said method comprises placing two protection devices for protection of a right and left joint.

16. The method, according to claim 15, wherein said two protection devices are interconnected by a securing means.

17. A method for hip stabilization comprising:
(a) positioning two protection devices lateral to each trochanter area of a body wherein said protection devices are interconnected with a securing means, and wherein each protection device comprises an outer rigid shield having an outer and inner face, a cushion comprising a plurality of cross-sectionally tiered pad components affixed to the inner face of said shield wherein said plurality of pad components comprises a first pad component centrally disposed on the inner face of said shield, a second pad component disposed around the periphery of said first pad component, and a third pad component disposed cranially to said first and second pad components, wherein said second pad component has a thickness greater than said first pad component wherein said second pad component directly contacts the wearer of said device, thereby holding said centrally disposed first pad component away from the wearer, and wherein said third pad component protrudes medially beyond the first and second components so as to apply pressure to a gluteus muscle of the wearer; and
(b) tightening the securing means around the pelvic area to stabilize the hip joint.

18. The method, according to claim 17, wherein said hip stabilization method reduces postural sway.

19. The method, according to claim 17, wherein said securing means is positioned across the hip to buttress the lumbopelvic arch.

20. The method, according to claim 17, wherein the securing means comprises a front belt and a back belt.

21. The method, according to claim 20, wherein the front belt is positioned higher than the back belt.

22. The method of hip stabilization, according to claim 17, wherein said device augments lateral abduction of the hip joint.

23. The method, according to claim 22, wherein said augmentation of lateral abduction is achieved by applying pressure to a gluteus medius muscle.

24. The method, according to claim 23, wherein said pressure to the gluteus medius muscle is applied by said third pad component.

* * * * *

UNITED STATES PATENT AND TRADEMARK OFFICE
CERTIFICATE OF CORRECTION

PATENT NO. : 5,437,618
DATED : August 1, 1995
INVENTOR(S) : W. David Sikes

It is certified that error appears in the above-indentified patent and that said Letters Patent is hereby corrected as shown below:

Column 1, line 56: Delete "Epiderniol" and insert --Epidemiol.--.

Column 4, line 22: Delete "fight trochanter" and insert --right trochanter--.

Column 7, line 65: Delete "flange 1" and insert --flange 2--.

Column 11, lines 5-6: Delete "to directly [contacts] contact" and insert --to directly contact--.

Column 12, line 3: Delete "second Fad" and insert --second pad--.

Signed and Sealed this

Fourteenth Day of November, 1995

*Attest:*

BRUCE LEHMAN

*Attesting Officer*     *Commissioner of Patents and Trademarks*